US009459084B2

(12) United States Patent
Towns et al.

(10) Patent No.: US 9,459,084 B2
(45) Date of Patent: Oct. 4, 2016

(54) APPARATUS FOR MEASURING AN ARTICLE

(71) Applicant: C & J CLARK INTERNATIONAL LIMITED, Street (GB)

(72) Inventors: Chris Towns, Taunton (GB); Peter Rickett, Englefield Green (GB); Dan Innes, London (GB); Yaan Kinally, Isleworth (GB)

(73) Assignee: C & J CLARK INTERNATIONAL LIMITED, Street, Somerset (GB)

( * ) Notice: Subject to any disclaimer, the term of this patent is extended or adjusted under 35 U.S.C. 154(b) by 0 days.

(21) Appl. No.: 14/945,998

(22) Filed: Nov. 19, 2015

(65) Prior Publication Data

US 2016/0069660 A1 Mar. 10, 2016

Related U.S. Application Data

(63) Continuation of application No. 14/232,541, filed as application No. PCT/GB2012/051615 on Jul. 9, 2012, now Pat. No. 9,228,817.

(30) Foreign Application Priority Data

Jul. 13, 2011 (GB) .................................... 1111997.1

(51) Int. Cl.
*G01B 5/02* (2006.01)
*A43D 1/02* (2006.01)
*G01B 3/10* (2006.01)
(Continued)

(52) U.S. Cl.
CPC ................. *G01B 5/025* (2013.01); *A43D 1/02* (2013.01); *A43D 1/08* (2013.01); *G01B 3/1084* (2013.01); *G01B 5/02* (2013.01); *A61B 5/1074* (2013.01)

(58) Field of Classification Search
CPC ..... G01B 5/02; G01B 5/0035; G01B 2210/58
USPC ...................................................... 33/759, 769
See application file for complete search history.

(56) References Cited

U.S. PATENT DOCUMENTS

| 263,971 | A | 9/1882 | Schaefer |
|---|---|---|---|
| RE14,409 | E | 12/1917 | Saxton |
| 2,146,799 | A | 2/1939 | Davis, Jr. |

(Continued)

FOREIGN PATENT DOCUMENTS

| GB | 2492805 A | 1/2013 |
|---|---|---|
| NL | 1011049 C2 | 7/2000 |

(Continued)

OTHER PUBLICATIONS

International Search Report dated Sep. 20, 2012 corresponding to International Patent Application No. PCT/GB2012/051615. per MPEP 609. Submitted in U.S. Appl. No. 14/232,541.

(Continued)

*Primary Examiner* — Yaritza Guadalupe-McCall
(74) *Attorney, Agent, or Firm* — Squire Patton Boggs (US) LLP

(57) ABSTRACT

There is provided a measuring device having a pair of pivoted arms, the ends of which remote from the pivot having an associated tape. The tape is fixed to one arm and extends internally through the other arm to be wound on to a biased reel located in a housing part, the reel taking up any slack in the tape.

17 Claims, 6 Drawing Sheets

(51) Int. Cl.
*A43D 1/08* (2006.01)
*A61B 5/107* (2006.01)

(56) References Cited

U.S. PATENT DOCUMENTS

| | | |
|---|---|---|
| 2,636,281 A | 4/1953 | Unger |
| 2,683,933 A | 7/1954 | McFarland |
| 4,265,021 A | 5/1981 | Campbell |
| 4,453,680 A | 6/1984 | Miller |
| 4,688,653 A | 8/1987 | Ruble |
| 5,062,215 A | 11/1991 | Schlitt |
| 5,174,030 A | 12/1992 | Clot et al. |
| 5,184,407 A | 2/1993 | Watrous |
| 5,193,287 A | 3/1993 | Coulter et al. |
| 5,367,785 A | 11/1994 | Benarroch |
| 5,371,949 A | 12/1994 | Delaurier |
| 5,430,951 A | 7/1995 | Jacky |
| 5,613,302 A | 3/1997 | Berman et al. |
| 6,209,213 B1 | 4/2001 | Moe |
| 6,253,459 B1 | 7/2001 | Barnhill |
| 6,598,310 B1 | 7/2003 | Odachowski |
| 6,640,460 B1 | 11/2003 | Nabarro et al. |
| 6,817,110 B2 | 11/2004 | Bohnengel |
| 6,978,553 B2 | 12/2005 | Doublet |
| 7,047,659 B2 | 5/2006 | Holland |
| 7,146,743 B2 | 12/2006 | Oura |
| 7,552,538 B1 | 6/2009 | Bushman et al. |
| 8,146,261 B1 | 4/2012 | Perry |
| 2002/0184779 A1 | 12/2002 | Bohnengel |
| 2012/0266479 A1 | 10/2012 | Park |
| 2014/0196301 A1* | 7/2014 | Towns ............ A43D 1/02 33/769 |

FOREIGN PATENT DOCUMENTS

| | | |
|---|---|---|
| SU | 1188510 A1 | 10/1985 |
| WO | WO2011/071298 A2 | 6/2011 |

OTHER PUBLICATIONS

Examination Report dated Dec. 17, 2015 corresponding to Saudi Arabia patent application No. 112330690.

* cited by examiner

APPARATUS FOR MEASURING AN ARTICLE

CROSS REFERENCE TO RELATED APPLICATIONS

This is a Continuation of U.S. patent application Ser. No. 14/232,541 filed on Feb. 24, 2014 which is a 371 of International Patent Application No. PCT/GB2012/051615 filed Jul. 9, 2012, which designates the U.S. and was published under PCT Article 21(2) in English, and which claims priority from United Kingdom Patent Application No. 1111997.1, dated Jul. 13, 2011. The contents of these applications are hereby incorporated by reference.

BACKGROUND

Field

The present invention relates to apparatus for measuring an article, particularly but not exclusively for measuring the girth or partial girth of an article. The apparatus finds particular use in measuring the girth of a foot for correct fitting of footwear.

SUMMARY

According to the present invention there is provided apparatus for measuring an article, the apparatus comprising: a pair of arms which are movable with respect to each other about a pivot, each arm having an end remote from the pivot; a flexible, elongate measuring element associated with the ends of the arms such that the measuring element has one extremity fixed with respect to the end of one arm and is able to move relative to a guide provided at the end of the other arm, the other extremity of the measuring element being secured to a reel which is biased to take up any slack in the measuring element.

Preferably, the other ends of the arms are each attached to respective cooperating housing parts which are rotatable relative to each other and which incorporate the pivot, the reel being coaxial with the pivot and free to rotate relative to both housing parts.

In preferred arrangements said other arm has an internal passage through which the measuring element can move, the passage opening at the free end of said other arm remote from the pivot to constitute said guide and leading at the pivot end of the arm to said reel.

Conveniently, the two arms are generally L-shaped and face in opposite directions, the two ends remote from the pivot abutting each other and also the end of each arm remote from the pivot tapers inwardly.

Normally the measuring element is in the form of a tape.

It is a preferred feature that biasing means urges the ends of the two arms towards each other and usually the biasing means for the two arms also biases the reel. The biasing action may utilise a clockspring.

A useful feature is that the reel includes a holding mechanism for locking the measuring element when a measurement is to be taken.

In preferred embodiments the reel incorporates a digital measuring device for measuring the length of measuring element paid out relative to said guide when the ends of the two arms are moved apart and said article is being measured, the digital measuring device having a display for indicating the length of measuring element paid out.

In further preferred arrangements the digital measuring device also measures the angular displacement of the arms in order to calculate the linear distance between the free ends of the arms, this linear distance being capable of being shown on the display.

BRIEF DESCRIPTION OF THE DRAWINGS

Embodiments of the invention will now be described in more detail. The description makes reference to the accompanying drawings in which.

DETAILED DESCRIPTION OF THE PREFERRED EMBODIMENT(S)

Figure 1:
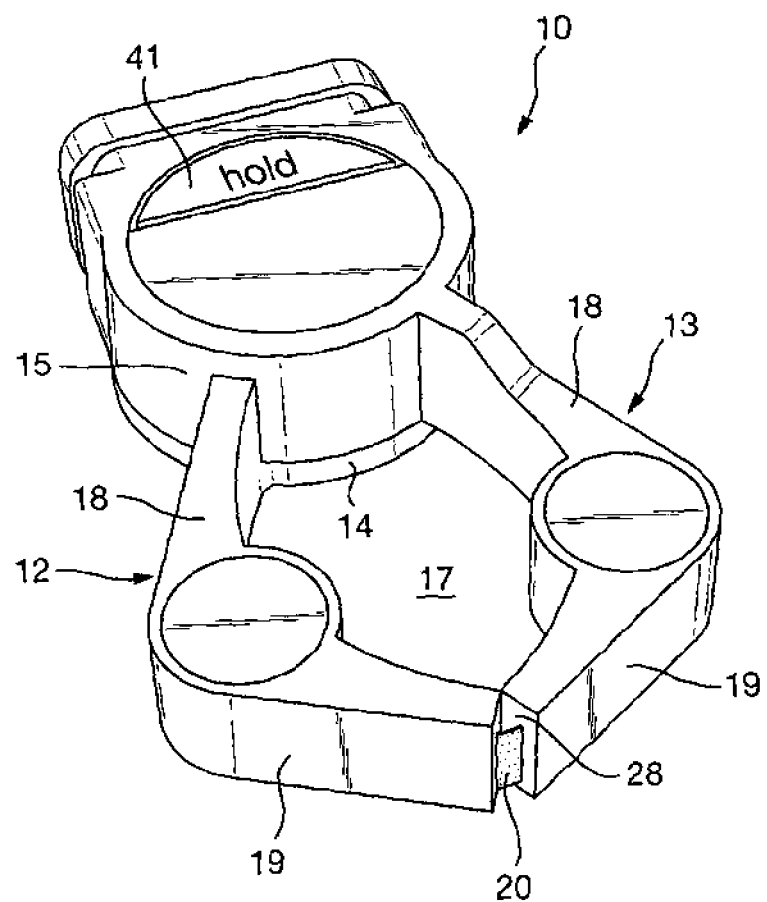
FIG. 1 is a perspective view of a measuring device according to the present invention.

In the figures there is shown a measuring device 10 which is particularly useful for measuring the girth of a foot 11 although the device 10 can be used for measuring the girth or partial girth of other objects and can also be used to measure linear distances. When measuring girth for footwear, the person usually stands on the floor and the girth measurement is taken from one side of the foot where it meets the floor and over the top of the foot to the other side of the floor where it meets the floor. This is indicated more clearly in FIG. 5.

The device 10 has a pair of arms 12, 13. One of the arms 12 is attached to a rear housing part 14 and the other arm 13 is attached to a forward housing part 15. The two housing parts 14, 15 are connected together so as to be rotatable relative to each other about a central pivot 16. Other housing constructions are possible provided the two arms are able to pivot relative to each other.

Figure 5A:
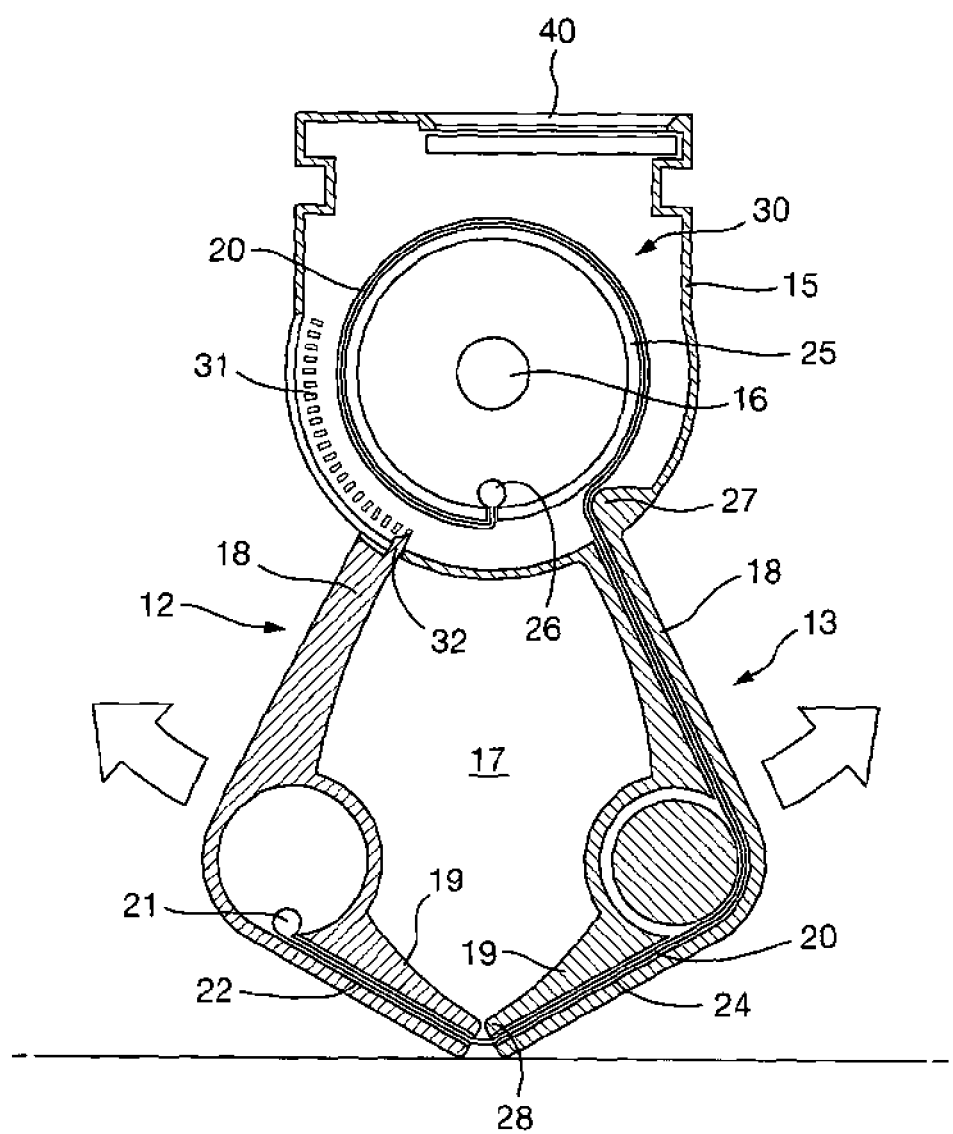
FIG. 5a is a vertical section through the measuring device of FIG. 1 not in use.

In the illustrated arrangement the two arms 12, 13 are generally L-shaped but oppositely disposed so as to leave a space 17 between the two arms, which space 17 can be beneficial when measuring the girth of certain articles. The 'upright' part 18 of each L-shaped arm 12, 13 is generally aligned with the pivot 16 such that the 'lower' part 19 of each L-shaped arm 12, 13 is somewhat angled relative to the floor. Ideally the two arms 12, 13 are biased towards each other by suitable biasing means such as a clockspring (not shown) so that the free ends of the lower parts 19 abut as illustrated in FIGS. 1 and 5a when in an 'at rest' position. Other arm shapes would of course be possible depending somewhat on the end use of the device 10.

The measuring device 10 includes a flexible, elongate measuring element 20 which is in the form of a length of tape in the illustrated embodiment but could take another form such as a cord. One extremity 21 of the tape 20 is fixed with respect to said one arm 12 and in the illustrated embodiment the tape 20 extends along an internal passage 22 and the extremity 21 is held internally in a hollow section 23 of the arm 12 where the two parts 18, 19 of the L-shape meet.

The tape 20 also passes through another internal passage 24 in the other arm 13 and extends the full length of the arm 13 to the housing 14, 15 where it is attached to a reel 25 at location 26. The reel 25 is rotatably mounted on the pivot 16 and is biased in an anti-clockwise direction by a biasing means such as a return spring (not shown) for example so as to take up any slack in the tape 20. The forward housing part 15 also incorporates an internal guide surface 27 to facilitate a smooth transition of the tape 12 between the arm 13 and the reel 25.

The free ends of the two arms 12, 13 are tapered so as to be generally pointed and the extreme free end 28 of the other arm 13 constitutes a simple guide for movement of the tape 20 during use. More complicated guides could be devised if desired. The pointed form of the free ends of the two arms 12, 13 enables the arms to abut closely when at rest and to enable access to tight spaces when in use, such as when positioned below a foot which tends to overhang the contact points with the floor or other supporting surface. The extreme free ends of the arms 12, 13 constitute the measurement reference points.

Figure 2:
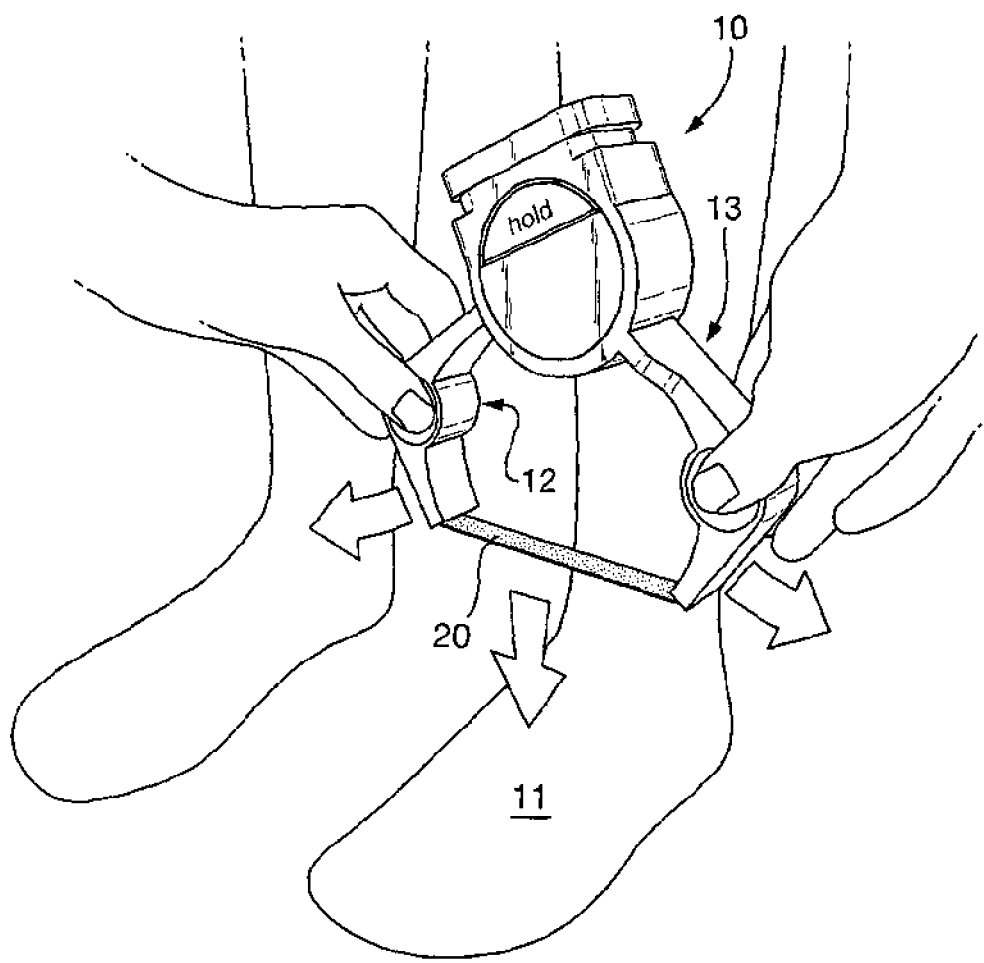
FIG. 2 is a perspective view of the measuring device of FIG. 1 about to be used to measure the girth of a foot.
Figure 3:
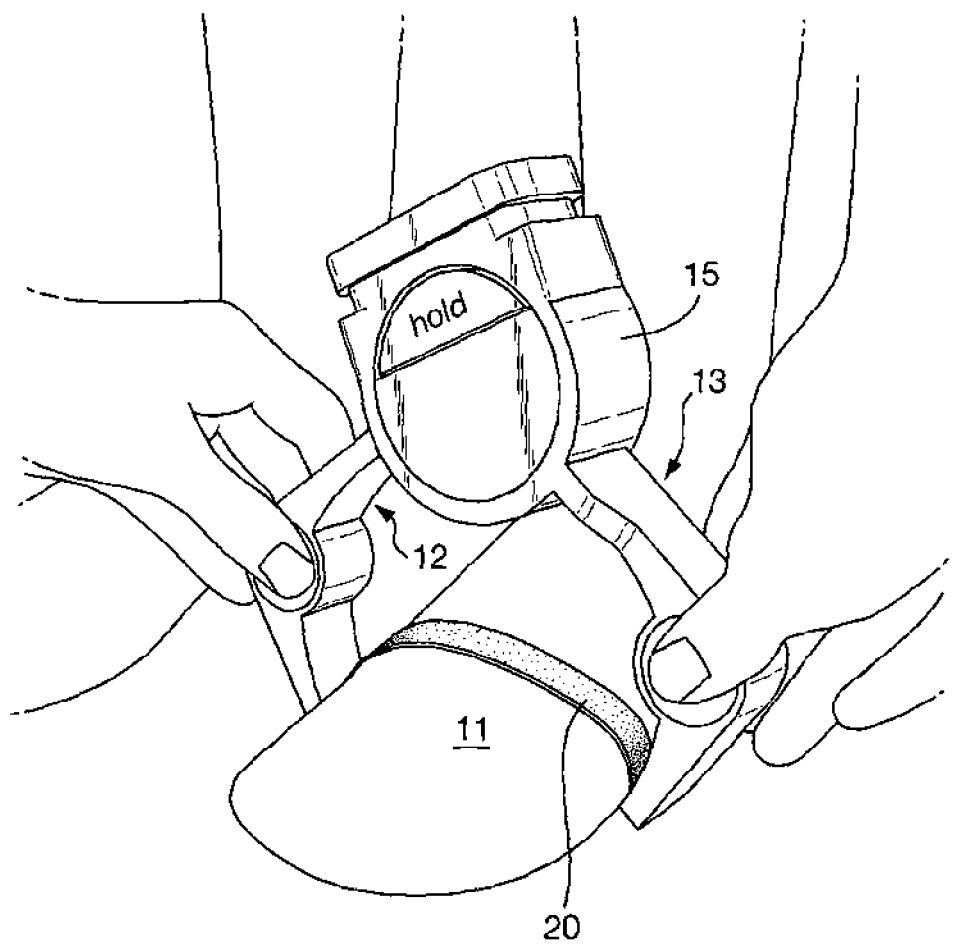
FIG. 3 is a perspective view of the measuring device of FIG. 1 in position relative to the foot.
Figure 4:
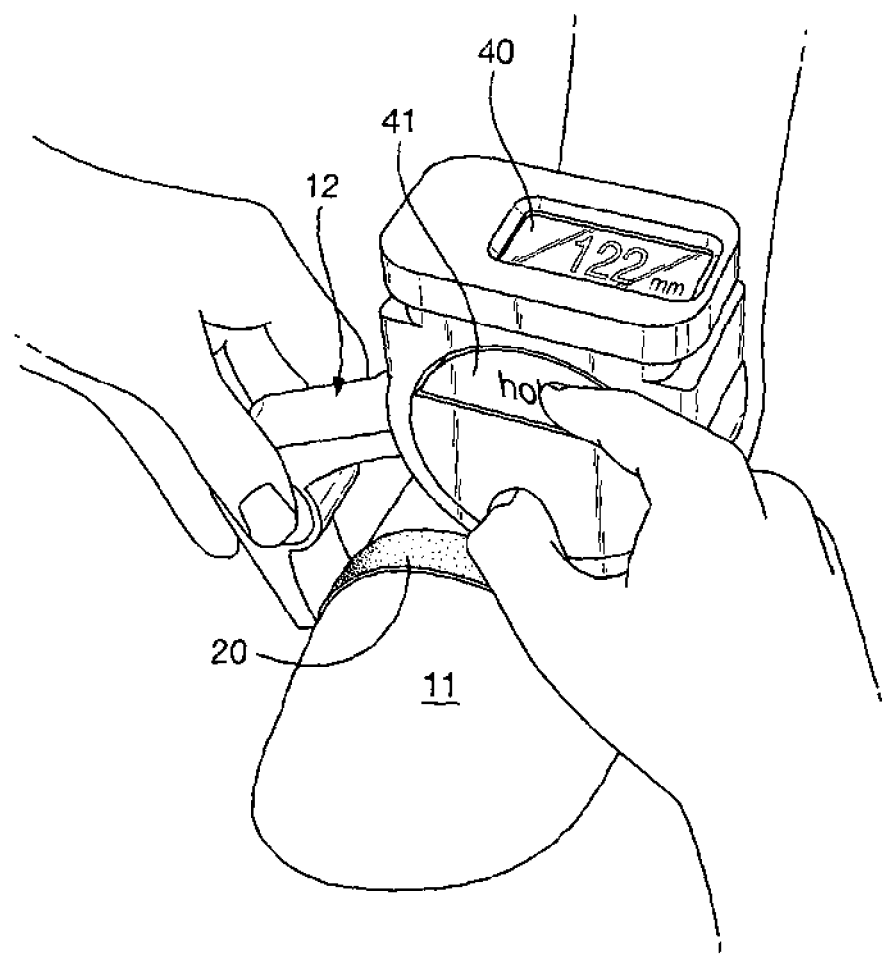
FIG. 4 is a perspective view of the measuring device of FIG. 1 showing a measurement being taken.

The housing parts 14, 15 also accommodate a digital measuring arrangement 30. Digital measuring arrangements are known but have been adapted for the present use. As an example, one form of digital measuring device 30 provides a digital scale 31 associated with the forward housing part 15 and an actuator 32 associated with said one arm 12. When the two arms 12, 13 are rotated relative to each other, i.e. opened up as shown in FIG. 2, tape 20 is paid out as the reel 25 rotates clockwise relative to the forward housing part 15 against the biasing force and the tape 20 extends in a generally straight line between the free ends of the two arms 12, 13. Movement of the two arms 12, 13 relative to each other results in the actuator 32 moving around the digital scale 31. The linear distance between the free ends of the arms is a function of the movement of the actuator 32 along the digital scale 31 which is calibrated to give a length output. The angular separation X of the two arms relative to the closed position, combined with the known distance from the arm ends to the pivot axis enables this linear distance to be calculated using software.

Figure 5B:
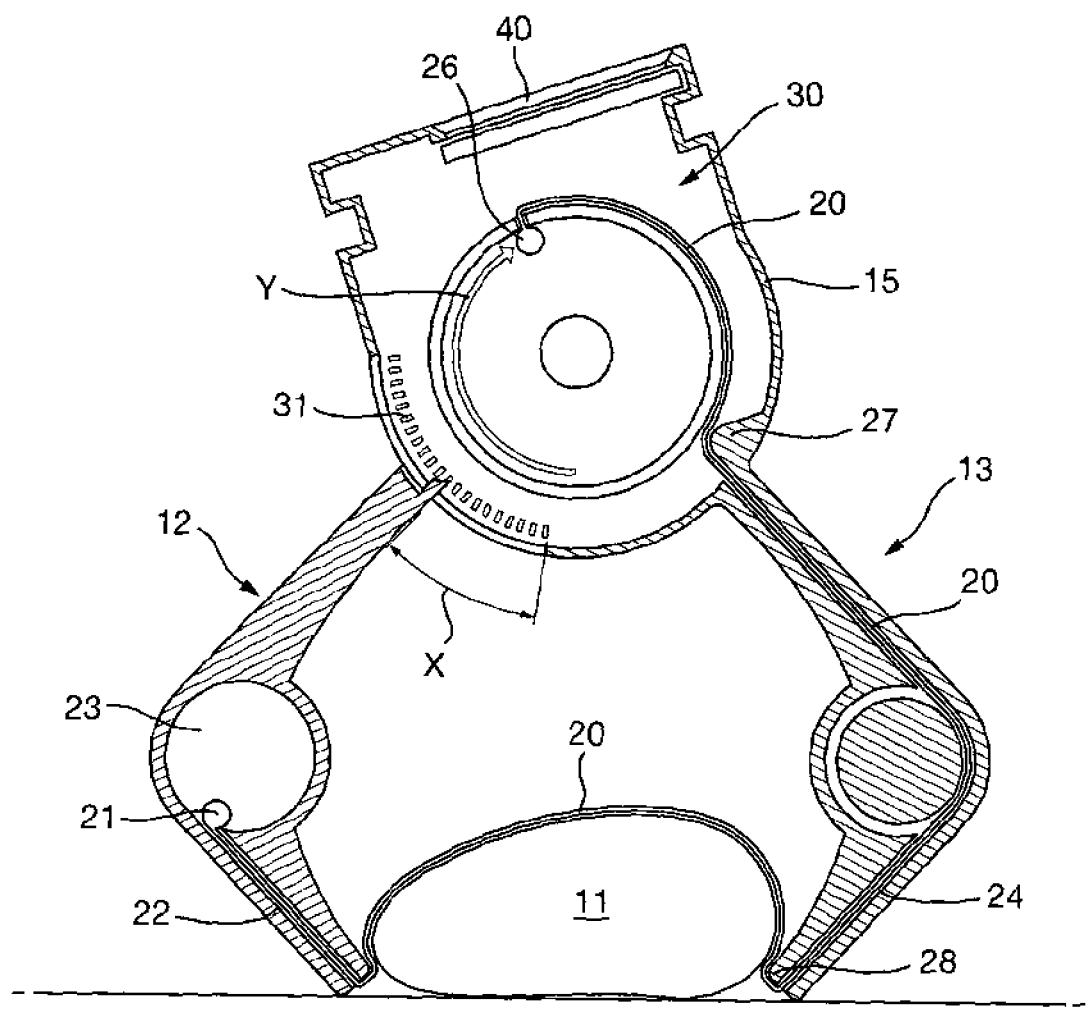
FIG. 5b is a vertical section through the measuring device of FIG. 1 in use measuring a foot.

When the device is placed around a three dimensional object, such as a foot 11 in FIG. 5b, more tape 20 is paid out by the drum 25 so as to follow the contour of the foot. The free ends of the two arms 12, 13 which constitute the measurement reference points, are moved into their correct positions below the lateral overhangs of the foot 11 as shown in FIG. 5. The length of tape 20 between the two free ends of the arms 12, 13 is the "over the foot" girth measurement that is required and the linear distance between the free ends of the arms is known as the tread width.

The clockwise rotation of the reel 25 against the biasing action causes any unwanted slack in the tape 20 to be taken up so as to ensure correct measurement. The rotation Y of the reel 25 gives a measure of the total amount of tape 20 which has been dispensed, this amount being a measure of the distance over the top of the foot from floor to floor. Again calibration of the digital measuring arrangement 30 together with the known reel dimensions is such that an output is provided for the total length of tape 20 between the two measurement reference points.

In addition, it is preferable for the software of the digital measuring arrangement 30 to provide a total girth or circumference measurement by means of an addition of the tread width, i.e. the linear distance between the ends of the arm (measured by the relative angular displacement of the arms) and the "over the foot" measurement (measured by the amount of tape 20 dispensed by the reel). This total girth measurement in a "weight on" condition, coupled with the other measurements gives a true indication of foot width/girth dimensions for improved shoe fitting.

The digital measuring arrangement 30 can, in preferred arrangements, take the following form although other methods are possible within the scope of the invention. A radially extending set of resistive electro contacts are located on the side of the tape reel 25 and these contacts bridge a circular array of contacts located on a static PCB (Printed Circuit Board). When the arms 12, 13 are closed, the contacts provide a zero reading but as the arms are opened and tape 20 is dispensed, the relative movement of the reel contacts and the PCB contacts relays a value of the length of tape dispensed as the reel rotates.

The device 10 also incorporates a display screen 40 which displays the total length of tape 20 paid out and also a 'hold' button 41. The hold button 41 is pressed when the arms 12, 13 are in their correct measuring position. The button 41 effectively locks movement of the reel 25 relative to the housing 14, 15 so that the total length displayed on the screen 40 can be set when the arms are correctly positioned. This can be beneficial if the foot belongs to someone prone to movement, such as a child. The locking action of the reel 25 can be by simple means such as the button engaging the reel to prevent rotation.

The precise design of the measuring device is open to modification whilst remaining within the scope of the claims. In its simplest form, the tape 20 could have measurements printed thereon and the digital measuring arrangement 30 could be omitted.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A method for measuring a three dimensional object by a measurement apparatus comprising a pair of arms and an elongate measuring element extending between the arms, the measuring element having at least one extremity secured to a reel and being biased to take up slack therein, the method comprising:
    placing the measurement apparatus around the three dimensional object by moving the arms relative to each other about a pivot to place the three dimensional object between the arms while placing the measurement element extending between the arms against the three dimensional object so that the measurement element follows a contour of the three dimensional object; and
    determining at least one measurement of the three dimensional object based on a length of the measurement element paid out from the reel or rotation of the reel, and an angular relative displacement of the arms.

2. The method according to claim 1, wherein the reel rotates on the pivot and the reel is biased to take up slack in the measurement element.

3. The method according to claim 1, said method further comprising determining a girth measurement based on rotation of the reel or the amount of measurement element paid out from the reel or a tread width based on the distance between the free ends of the arms.

4. The method according to claim 1, further comprising determining a measurement based on a linear distance between free ends of the aims measured by the relative angular displacement of the aims and amount of measurement element dispensed by the reel or rotation of the reel.

5. The method according to claim 1, wherein the measuring element comprises a tape.

6. A computer program embodied on a non-transitory computer-readable medium, said computer program comprising program code configured to perform the method of claim 1 when the program is run on a processor.

7. The method according to claim 1, wherein the at least one extremity secured to the reel is coaxial with the pivot of the arms.

8. An apparatus for measuring three dimensional objects, the apparatus comprising:
- a pair of aims moveable relative to each other about a pivot and configured to receive a three dimensional object there-between;
- an elongate measuring element extending between the aims and biased to take up slack therein; and
- a reel, wherein the measuring element has one extremity secured to the reel so that when the measurement element extending between the arms is placed against the three dimensional object between the aims so that the measurement element follows the contour of the three dimensional object the reel rotates, and
- wherein the at least one measurement of the three dimensional object is based on the length of the measurement element paid out from the reel or rotation of the reel, and an angular relative displacement of the arms.

9. An apparatus according to claim 8, wherein the arms are generally L-shaped and face in opposite directions, the free ends of the aims remote from the pivot abutting each other.

10. An apparatus according to claim 8, wherein the reel is rotatable on the pivot and biased to take up slack in the measurement element.

11. An apparatus according to claim 8, configured to determine a girth measurement based on rotation of the reel or the amount of measurement element paid out from the reel or a tread width based on the distance between the free ends of the arms.

12. An The apparatus according to claim 8, wherein the measuring element comprises a tape.

13. The apparatus according to claim 8, wherein the means for determining comprises a digital measurement device for measuring the length of measuring element paid out or rotation of the reel when the ends of the aims are moved apart and said object is being measured, the digital measuring device comprising a display for indicating measurements.

14. The apparatus according to claim 8, further comprising biasing means for urging the ends of the aims towards each other and for biasing the reel and the measurement element attached thereto.

15. The apparatus according to claim 8, comprising a holding mechanism for locking the measuring element when a measurement is to be taken.

16. The apparatus according to claim 8, wherein the at least one extremity secured to the reel is coaxial with the pivot of the arms.

17. An apparatus for measuring three dimensional objects, the apparatus comprising:
- a pair of arms moveable relative to each other about a pivot and configured to receive a three dimensional object there-between;
- an elongate measuring element extending between the arms and biased to take up slack therein; and a reel, wherein the measuring element has one extremity secured to the reel so that when the measurement element extending between the arms is placed against the three dimensional object between the arms so that the measurement element follows the contour of the three dimensional object the reel rotates,
- wherein the at least one measurement of the three dimensional object is based on the length of the measurement element paid out from the reel or rotation of the reel, or an angular relative displacement of the arms,
- wherein the apparatus is configured to determine a measurement based on a linear distance between the free ends of the arms measured by the relative angular displacement of the aims and amount of measurement element dispensed by the reel or rotation of the reel.

* * * * *